United States Patent [19]

Kobayashi et al.

[11] 4,280,834
[45] Jul. 28, 1981

[54] NOVEL DIPHENYL ETHER DERIVATIVE AND HERBICIDAL COMPOSITION CONTAINING THE SAME AS AN ACTIVE COMPONENT

[75] Inventors: Kenji Kobayashi, Ageo; Katuhiko Hibi, Fukiage; Hisabumi Kobayashi; Shoichi Kato, both of Ageo, all of Japan

[73] Assignee: Nippon Kayaku Kabushiki Kaisha, Tokyo, Japan

[21] Appl. No.: 123,025

[22] Filed: Feb. 20, 1980

[30] Foreign Application Priority Data

Mar. 9, 1979 [JP] Japan .................. 54-26631

[51] Int. Cl.$^3$ .................. A01N 41/10; C07C 147/06
[52] U.S. Cl. .................. 71/103; 568/33
[58] Field of Search .................. 71/103; 568/33

[56] References Cited

U.S. PATENT DOCUMENTS 4,023,958  5/1977  Rohe et al. .................. 71/103

FOREIGN PATENT DOCUMENTS 50-40729  4/1975  Japan .................. 71/103
50-53525  5/1975  Japan .................. 71/103

*Primary Examiner*—Glennon H. Hollrah
*Attorney, Agent, or Firm*—Wegner & Bretschneider

[57] ABSTRACT

Disclosed herein are a novel compound, 3-n-propylsulfonylphenyl 4'-trifluoromethylphenyl ether and a herbicide composition containing the same as an active ingredient.

3 Claims, No Drawings

NOVEL DIPHENYL ETHER DERIVATIVE AND HERBICIDAL COMPOSITION CONTAINING THE SAME AS AN ACTIVE COMPONENT

DETAILED DESCRIPTION OF THE INVENTION

The present invention concerns 3-n-propylsulfonylphenyl 4'-trifluoromethylphenyl ether:

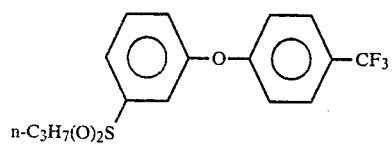

and a herbicidal composition containing the same as an active ingredient.

Hitherto, herbicides containing various derivatives of diphenyl ether have been known. For instance, in Japanese Patent Application Laying Open No. 53525/1975, 3-n-propylsulfinylphenyl 4'-trifluoromethylphenyl ether and 3-n-propylthiophenyl 4'-trifluoromethylphenyl ether are disclosed as the active component of herbicidal compositions. However, these publicly known compounds do not show sufficient herbicidal effect against *Sida spinosa, Commelina communis, Vicia sativa*, etc. which have been hardly controlled by conventional herbicides.

The invention of the present invention, after examination of various new herbicidal compounds, have completed the present invention. The compound of the present invention shows an excellent herbicidal effect against the above-mentioned species of weeds at a small dosage, and is able to completely control the broad-leaf weeds of the families of Caryophyllaceae, Cruciferae, Compositae, etc. and also graminaceous weeds such as *Echinochloa crus-galli, Digitaria adscendens*, etc. without causing any damage on soybean, peanut, corn, cotton, wheat, etc. which are the major crop plants in the upland fields.

The compound of the present invention is possibly synthesized, for example, by the following route:

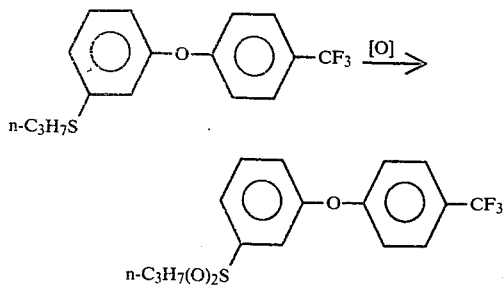

That is, 3-n-propylsulfonylphenyl 4'-trifluoromethylphenyl ether (II) is obtainable by reacting 3-n-propylthiophenyl 4'-trifluoromethylphenyl ether (I) with a suitable oxidant in a suitable solvent at a temperature of 0° to 120° C.

As the suitable oxidants there can be mentioned for example, a hydroperoxide such as hydrogen peroxide, an organic peroxide such as peracetic acid and perbenzoic acid, fuming nitric acid, a permanganate such as potassium permanganate, a persulfate such as potassium persulfate and these are possibly used to give a favorable result by the amount of 1.0 to 4.0 times of the theoretical amount. As the suitable solvents, any one which do not concern the above-mentioned reaction can be used, however, acetic acid is preferably used, and when other solvents are used in the reaction, the presence of acetic acid in an amount more than the amount of the starting compound (I) is preferable. When the oxidation is carried out by adding sulfuric acid on a salt of persulfuric acid, the economic value is extremely high because of the feasibility of the reaction in an aqueous solution.

The period of time of the reaction differs depending on the kinds of the oxidants, however, usually 0.5 to 3 hours may be enough.

The compound of the formula (II) of the present invention can be also synthesized by the following method: That is, the compound of formula (II) is obtainable by condensing the alkali salt of the compound of the formula:

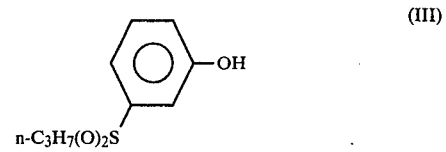

with the compound of the formula:

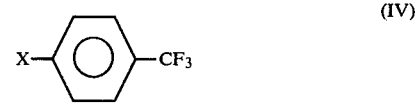

wherein X is chloro or hromo in suitable solvent, for example, dimethylformamide or dimethyl acetamide at a temperature of, for example, 70°–165° C. In the above condensation, it may be possible that ① the alkali salt of formula (III) is firstly prepared and then said salt is reacted with the compound of formula (IV) or ② the reaction is conducted under the coexistence of the compound of formula (III), alkaline compound and the compound of formula (IV). As the alkaline compounds, there may be mentioned for example, pottasium hydroxide or sodium hydroxide.

The following are the explanation in detail of the present invention referring to Example:

PREPARATION EXAMPLE 1

Into 50 ml of acetic acid, 2.5 g (0.008 mole) of 3-n-propylthiophenyl 4'-trifluoromethylphenyl ether were added and dissolved under agitation. While cooling the thus prepared solution at a temperature below 10° C., 20g (0.018 mole) of an aqueous 30% solution of hydrogen peroxide were added to the cooled solution, and after making the reaction proceed for about one hour at room temperature the reaction mixture was heated to 80° to 90° C. for about one hour. After cooling, the reaction mixture was poured into iced water, and the oily substance was extracted with benzene. After washing the benzene layer with water and then drying with anhydrous sodium sulfate, the benzene was distilled off to leave a solid. By recrystallizing the solid with a mixture of n-hexane and ethyl acetate, 2.5 g of yellow-coloured crystalline 3-n-propylsulfonylphenyl 4'-trifluoromethyl ether (yield 90.7%) were obtained. The crystal showed a melting point of 89° to 89.5° C. The elementary analysis of the crystal gave the data of: C of 55.57% and H of 4.18%, while calculation as $C_{16}H_{15}F_3O_3S$, gave: C of 55.81% and H of 4.39%.

PREPARATION EXAMPLE 2

Into 20 ml of N,N-dimethylformamide, 5 g of 3-n-propylsulfonyl phenol of the formula:

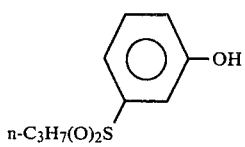

were added. Then 1.6 g of pottasium hydroxide is added to the above mixture under stirring and then heated to produce the pottasium salt of the said phenol. After cooling to about 50° C., 5.4 g of 4-trifluoromethyl chlorobenzene were added to the reaction mixture. Then the whole was refluxed for 40-60 hrs. After cooling, when the reaction mixture was poured into a 5% aqueous sodium hydroxide solution, the crystals were precipitated. And the crystals were washed with water dried and recrystalized from methanol, then 3-n-propylsulfonylphenyl 4'-trifluoromethylphenyl ether was obtained.

The compound of the present invention is usually used after mixing with various types of carriers. The solid carriers include for example, clay, caoline, talc, diatomaceous earth, silica, calcium carbonate, saw dust, etc. and the liquid carriers include organic solvents, for example, benzene, alcohol, acetone, xylene, methylnaphthalene, cyclohexane, dimethylformamide, dimethylsulfoxide, animal and vegetable oils, fatty acids, esters of fatty acids, etc. and various surface active agents, etc.

The effects of the compound of the present invention are possibly enhanced or stabilized by admixing one or more than two kinds of adjuvants which are usually used for agricultural chemicals, for instance, spreaders, stickers, wetting agents, collapsing agents, etc. other than carriers. Moreover, the compound of the present invention is possibly used after blended with other pesticides and agricultural chemicals, for example, insecticides, fungicides, bactericides, nematocides, herbicides, plant-growth controlling agents, soil-improving matters or fertilizers, etc.

The herbicidal composition containing the compound of the present invention as an active ingredient is applied in the forms of dusts, fine granules, granules, wettable powders, solutions, etc. The content of the active ingredient, i.e., the compound of the present invention in the herbicidal composition of the present invention differs depending on the formulations, and in some cases, solely the active ingredient itself is used, however, usually it is 0.5 to 95%, preferably in the range of 2 to 50% by weight. The amount of the carrier and the other adjuvants is 5 to 99.5%, preferably 50 to 98% by weight.

In the case where herbicidal operation is carried out by applying the herbicide of the present invention, the dosage, i.e., the amount applied per are of the field depends upon the states of the field, however, usually it is 2 to 100 g of the active ingredient, i.e., the compound of the present invention, per are, preferably 5 to 50 g.

The following are the explanations of the herbicidal composition of the present invention by Examples of formulation. In addition, the term "part"herein used means the part by weight.

EXAMPLE FOR FORMULATION 1

Ten parts of the compound of the present invention, 45 parts of talc and 45 parts of clay were mixed and pulverized to be a dust which is to be scattered on its application as it is.

EXAMPLE FOR FORMULATION 2

Twenty parts of the compound of the present invention, 60 parts of caoline and 17 parts of diatomaceous earth were mixed well, and 1 part of a salt of alkylnaphthalenesulfonic acid and 2 parts of a salt of ligninsulfonic acid were admixed with the above-mentioned mixture and the whole amount was pulverized to be a wettable powder which is to be applied by spraying after suspending into water.

EXAMPLE FOR FORMULATION 3

Twenty parts of the compound of the present invention were dissolved into 63 parts of xylene, and 17 parts of polyoxyethylenealkylphenolether were admixed with the above-mentioned solution to be dissolved thereinto. This composition was used as emulsion after dilution with water.

EXAMPLE FOR FORMULATION 4

Three parts of the compound of the present invention, 35 parts of diatomaceous earth, 23 parts of bentonite, 37 parts of talc and 2 parts of a disintegrator were mixed well, and 18 parts of water were carefully added to the powdery mixture to wet the mixture uniformly. The thus wetted mixture was extruded by an injection molding machine to be wet granules, which were dried and then made uniform in size by a crusher to be granules. The granular herbicidal composition thus obtained was directly applied as it was.

EXAMPLE FOR FORMULATION 5

Thirty parts of the compound of the present invention, 40 parts of powdery hydrated silica and 20 parts of clay were mixed, and 10 parts of a mixture of sodium lauryl sulfate and sodium 2,2'-dinaphthylmethanesulfonate were admixed with the above-mentioned mixture uniformly, and then the whole material was pulverized to be a wettable powder. It was suspended into water and the suspension was applied by spraying.

The followings are the concrete explanations of the effectiveness of the present invention by Test Examples.

TEST EXAMPLE 1

A soil of an upland field was uniformly filled in plastic vessels, each of 25×40 cm in size, and seed of *Sida spinosa* as a representative of the plants belonging to the genus Sida against which a suitable herbicide has not been found and large efforts have been devoted to control in the cultivation of crops in upland field, and seeds of *Commelina communis* and *Vicia sativa* both of which are not effectively controlled by the conventional herbicides for use in upland fields were respectively sown at an fixed amount, and then the sown seeds were covered with the soil of 0.5 cm in thickness, and after lightly pressed the soil in the sown vessels was placed in a glass house after uniform watering. On the next day, herbicidal fluids diluted with water containing the compound of the present invention were uniformly scattered on the soil in the vessels at a rate of 10 liters/are in respective amounts such that the amounts of the compound applied on the soil of the field become respectively 6.25, 12.5 and 18.75 g/are when the fluid is applied on the soil. In similar manner, two conventional herbicidal fluid (of controls) were scattered onto the same kind of soil in other vessels. In the latter two cases (controls), the amounts of each one of the conventional herbicide were, respectively, 6.25, 12.5, 18.75, 25 and 50 g/are. The test had 2 replications. On the 20th day after the treatment, the weed-control effects were observed with the following standard on each species of the weeds. The results of examination are shown in Table 1 by the mean values of each two plots:

The standard of weed-controlling effects:

| Weed control Index | State of weed-control |
|---|---|
| 5 | completely killed the weed |
| 4 | 80% killed or controlled |
| 3 | 60% killed or controlled |
| 2 | 40% killed or controlled |
| 1 | 20% killed or controlled |
| 0 | not effective in killing or controlling the weed, being the same as in not-treated plot. |

TABLE 1

| Compound | Dosage (g/a) | Sida spinosa | Commelina communis | Vicia sativa |
|---|---|---|---|---|
| 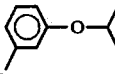 n-C₃H₇(O)₂S (of the present invention) | 18.75 | 5 | 5 | 5 |
| | 12.5 | 4 | 4 | 4 |
| | 6.25 | 3 | 3 | 3 |
| 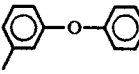 n-C₃H₇(O)S (positive control) | 50 | 4 | 5 | 5 |
| | 25 | 3 | 4 | 4 |
| | 18.75 | 2 | 2 | 3 |
| | 12.5 | 1 | 1 | 2 |
| | 6.25 | 0 | 0 | 1 |
| 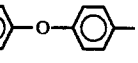 n-C₃H₇S (positive control) | 50 | 3 | 4 | 4 |
| | 25 | 2 | 3 | 3 |
| | 18.75 | 1 | 2 | 2 |
| | 12.5 | 1 | 1 | 2 |
| | 6.25 | 0 | 0 | 1 |
| Not-treated | — | 0 | 0 | 0 |

As is seen clearly in Table 1, the compound of the present invention showed an excellent herbicidal effect on *Sida spinosa* against which there has been no suitable herbicide and large efforts have been devoted to control, and only at the half or less dosage of the dosage of the compounds of positive control showed a sufficient weed-controlling effects not only against *Sida spinosa* but also against *Commelina communis* and *Vicia sativa*.

TEST EXAMPLE 2

In the same type of vatted soil of the upland field, each fixed amount of the seeds of graminaceous weeds of the upland fields such as *Setaria glauca, Panicum bisulcatum, Echinochloa crus-galli, Digitaria adscendens* and *Eleusine indica* was uniformly sown on the soil in the vessels and covered with the soil of 0.5 cm in thickness and after lightly pressed, uniformly watered. In another filled soil of the same type of the vessel, each fixed amount of the seeds of the representative weed of Compositae against which conventional herbicides of diphenyl ether-derivatives are not completely effective, such as *Galinsoga parviflora* and the seeds of major broad-leaf weeds in the upland fields such as *Amaranthus lividus, Chenopodium album* and *Polygonum nodosum* were sown uniformly and after covering with the soil of 0.5 cm in thickness and pressing lightly, uniformly watered. The above-mentioned vessels were put into a glass house and kept under the conditions of weed-growing at the season of summer crops. In the other experiment, in the same type and size of vessels, fixed amount of the soil was uniformly filled and then the soil containing the seeds of autumn to spring graminaceous weeds such as *Alopecurus aequalis* and *Poa annua*, the seeds of caryophyllaceous weeds (such as *Stellaria media* and *Stellaria uliginosa*) and the seeds of cruciferous weed (such as *Capsella bursa-pastoris*) which are not controllable completely with the conventional herbicides of diphenyl ether-derivatives were mixed with the soils of the above vessels in the depth of 0.5 cm, after tightly pressed uniformly watered. These vessels were kept in a glass house controlled at a temperature of 15° to 20° C. in order to controll the conditions to the growing conditions in autumn-winter crops.

On the next day of seed-sowing, herbicidal fluid, containing respectively the compound of the present invention at concentration which gave 6.25 and 12.5 g of the herbicide per are of the field plots, was sprayed uniformly on each the soil surface at 10 liter per are.

The test had 2 replications.

On the 20th day after the treatment, the weed-control effects were examined using the standard given in Test Example 1. The results are shown in Table 2, with the mean values.

TABLE 2

| | Dosage (g/a) of the compound of the present invention | | |
|---|---|---|---|
| Weed species | 12.5 | 6.25 | Not-treated |
| Gramineae | | | |
| Setaria glauca | 5 | 5 | 0 |
| Panicum bisulcatum | 5 | 5 | 0 |
| Echinochloa grus-galli | 5 | 4 | 0 |
| Digitaria adscendens | 5 | 5 | 0 |
| Eleusine indica | 5 | 5 | 0 |
| Alopecurus aequalis | 5 | 5 | 0 |
| Poa annua | 5 | 5 | 0 |
| Broad-leaf | | | |
| Galinsoga parviflora | 5 | 5 | 0 |
| Amaranthus lividus | 5 | 5 | 0 |

TABLE 2-continued

| Weed species | Dosage (g/a) of the compound of the present invention | | Not-treated |
|---|---|---|---|
| | 12.5 | 6.25 | |
| Chenopodium album | 5 | 4 | 0 |
| Polygonum nodosum | 5 | 4 | 0 |
| Stellaria media | 5 | 5 | 0 |
| Stellaria uliginosa | 5 | 5 | 0 |
| Capsella bursa-pastoris | 5 | 5 | 0 |

As is clearly seen in Table 2, against not only the weeds belonging to the families Caryophyllaceae, Compositae and Cruciferae but also against major weeds of Gramineae and broad-leaf weeds, the compound of the present invention shows an excellent herbicidal effect at a small dosage.

TEST EXAMPLE 3

The similar test was carried out as in Test Example 1 on the sown seeds of soybean, peanut, corn, cotton and wheat, however, covering the sown seeds with the soil of 1 cm in thickness and on the next day, the dosages of 100, 75, 50 and 25 g/are of the compound of the invention were applied respectively by uniform spraying on each the soil surface at 15 liters per are. The test had the replication of 2 times. On the 20th day after the treatment, the growth state of the plants in each plot was observed, and the growth state was recorded by the following standard:

| Mark | State |
|---|---|
| — | no effects on the growth of the plants |
| + | 20% chlorosis |
| + + | 40% chlorosis |
| + + + | 60% chlorosis |
| + + + + | 80% chlorosis |
| × | death |

The results are summarized in Table 3.

TABLE 3

| Compound | Dosage (g/are) | Soybean | Peanut | Corn | Cotton | Wheat |
|---|---|---|---|---|---|---|
| The compound of the present invention | 100 | ± | ± | + | — | + + |
| | 75 | — | — | ± | — | + |
| | 50 | — | — | — | — | — |
| | 25 | — | — | — | — | — |
| Not-treated | | — | — | — | — | — |

As is clearly seen in Table 3, even at the dosage as large as 8 to 10 times of the dosage at which herbicidal effect is expected the compound of the present invention gave no harm to the major crops in the upland fields. This fact shows the extreme safety of the compound of the present invention as an active ingredient of a herbicidal composition for use in the upland fields.

As has been described and shown in Tables 1 to 3, the compound of the present invention has an excellent herbicidal effectiveness against weeds of a broad range in the upland fields and also is quite safe to the crops in the upland fields and accordingly, the compound of the present invention possesses a quite desirable characteristic as a practical herbicide for use in the upland fields.

What is claimed is:

1. 3-n-propylsulfonylphenyl 4'-trifluoromethylphenyl ether.

2. An herbicidal composition which comprises an effective amount of 3-n-propylsulfonylphenyl 4'-trifluoromethylphenyl ether as an active ingredient, and a carrier and other adjuvants.

3. The herbicidal composition of claim 2 which comprises 0.5–95% by weight of 3-n-propylsulfonylphenyl 4'-trifluoromethylphenyl ether as an active ingredient and 99.5 to 5% by weight of the carrier and adjuvants.

* * * * *